United States Patent
Pilevar et al.

(10) Patent No.: US 6,558,958 B1
(45) Date of Patent: May 6, 2003

(54) OPTICAL FIBER EVANESCENT FIELD EXCITED FLUOROSENSOR AND METHOD OF MANUFACTURE

(75) Inventors: Saeed Pilevar, Gaithersburg, MD (US); Christopher C. Davis, Bowie, MD (US); Alexander J. Fielding, Beltsville, MD (US); Frank Portugal, Potomac, MD (US)

(73) Assignee: University of Maryland, College Park, MD (US)

(*) Notice: Subject to any disclaimer, the term of this patent is extended or adjusted under 35 U.S.C. 154(b) by 202 days.

(21) Appl. No.: 09/592,861

(22) Filed: Jun. 13, 2000

Related U.S. Application Data

(62) Division of application No. 08/866,080, filed on May 30, 1997, now Pat. No. 6,103,535.
(60) Provisional application No. 60/018,592, filed on May 31, 1996.

(51) Int. Cl.[7] .............................................. G01N 33/543
(52) U.S. Cl. ..................... 436/518; 385/12; 385/123; 422/58; 422/83; 422/82.05; 422/82.08; 422/82.11; 427/2.11; 427/2.12; 427/2.13; 427/162; 427/163.1; 427/163.2; 435/4; 435/5; 435/6; 435/7.4; 435/7.32; 435/287.1; 435/287.2; 435/288.7; 435/808; 436/164; 436/172; 436/527; 436/805
(58) Field of Search ..................... 385/12, 123; 422/58, 422/83, 82.05, 82.08, 82.11; 435/4, 5, 6, 7.4, 7.32, 287.1, 287.2, 288.7, 808; 436/164, 172, 518, 527, 805; 427/2.11, 2.12, 2.13, 162, 163.1, 163.2

(56) References Cited

U.S. PATENT DOCUMENTS

| | | |
|---|---|---|
| 4,447,546 A | 5/1984 | Hirschfeld |
| 4,654,532 A | 3/1987 | Hirschfeld |
| 4,834,496 A | 5/1989 | Blyler, Jr. et al. |
| 4,909,990 A | 3/1990 | Block et al. |
| 5,061,857 A | 10/1991 | Thompson et al. |
| 5,082,630 A | 1/1992 | Pertin et al. |
| 5,262,638 A | 11/1993 | Egalon et al. |
| 5,288,996 A | 2/1994 | Betzig et al. |
| 5,340,715 A | 8/1994 | Slovacek et al. |
| 5,344,784 A | 9/1994 | Attridge |
| 5,430,813 A | 7/1995 | Anderson et al. |
| 5,444,803 A | 8/1995 | Kim et al. |
| 5,485,277 A | 1/1996 | Foster |
| 5,525,466 A | 6/1996 | Slovacek et al. |
| 5,532,493 A | 7/1996 | Hale et al. |

FOREIGN PATENT DOCUMENTS

| | | |
|---|---|---|
| EP | 0 126 600 | 11/1984 |

OTHER PUBLICATIONS

Anderson, G., Ligler, F. et al., "Development of an Evanescent Wave Fiber Optic Biosensor", *IEEE Engineering in Medicine and Biology*, Jun./Jul., pp. 358–363, 1994.

Graham, Leslie, and Squirrel, "Gene Probe Assays on a Fiber–Optic Evanescent Wave Biosensor", *Biosensors and Bioelectronics*, p. 487, vol. 7, 1992.

(List continued on next page.)

*Primary Examiner*—Christopher L. Chin
(74) *Attorney, Agent, or Firm*—Millen, White, Zelano & Branigan, P.C.

(57) ABSTRACT

An optical fiber is tapered, preferably adiabatically, and has a material coated on it for chemical bonding with fluorophores. When the fluorophores couple with the material, evanescent radiation generated fibers causes the fluorophores to fluoresce, and the fluorescence is coupled back into the fiber.

38 Claims, 9 Drawing Sheets

OTHER PUBLICATIONS

Kronick and Little, "A New Immunoassay Based on Fluorescence Excitation by Internal Reflection Spectroscopy," *J. I. Immunological Methods*, p. 235, vol. 8, 1975.

Stewart, G., Norris, J., Clark, D.F., Tribble, M., Andonovic, J. and Culshaw, B., "Evanescent Wave Chemical Sensors: A Theoretical Approch", *Int. Jl, Optoelectronics*, vol. 6(3), pp. 227–238, 1991.

Vaez–Iravani, M. and Toledo–Crow, R., "Phase contrast and amplitude pseudoheterodyne–interference near field scanning optical microscopy," *Appl. Phys. Lett.*, vol. 62, No. 10, Mar. 8, 1993.

Kwong, N.S.K. and Lau, K., "Superluminescent Optical Sources for Sensor Applications," Optical Fiber Rotation Sensing, Academic Press, Inc., 1994, pp. 261–301.

OPTICAL FIBER EVANESCENT FIELD EXCITED FLUOROSENSOR AND METHOD OF MANUFACTURE

REFERENCE TO RELATED APPLICATIONS

This is a division of application Ser. No. 08/866,080 filed on May 30, 1997, which issued as U.S. Pat. No. 6,103,535. This application claims the benefit of U.S. Provisional Application No. 60/018,592, filed May 31, 1996 whose disclosure is hereby incorporated by reference in its entirety into the disclosure of this application.

FIELD OF THE INVENTION

The current invention relates to a global class of optical sensors that use evanescent fields to excite fluorescence from species bound to a waveguide fiber surface during assay performed in the gas phase, liquid solution, or solid environment.

DESCRIPTION OF RELATED ART

The evanescent field associated with an electromagnetic field propagating in an optical waveguide typically penetrates from a few nanometers to several hundred nanometers into the medium surrounding the optical waveguide. This evanescent field can excite fluorescent materials, such as fluorophores, which will fluoresce when they are bound by molecules on or very close to the optical waveguide surface. This fluorescence can lead to an efficient and selective immunoassay or hybridization assay. For an archetypal immunoassay sensor, biological recognition (binding) of an antigen by antibodies attached to the waveguide surface with concomitant displacement of fluorescent-labeled antigen is measured as a change in fluorescence. An oligonucleotide (either RNA or DNA), to which is attached a suitable fluorophore, is recognized by a complementary oligonucleotide (either RNA or DNA).

For a hybridization assay sensor, biological recognition (binding) of an oligonucleotide is measured as a change in fluorescence. A suitable fluorophore is attached to the oligonucleotide by a complementary oligonucleotide (either RNA or DNA) that in turn is attached to the waveguide surface, with a concomitant enhancement of fluorescence.

The use of optical fibers in certain geometrical configurations for immunoassay sensors is also known. One such use of optical fibers is as waveguides that capture and conduct fluorescent radiation emitted by molecules near the optical fiber surface. However, waveguide-binding sensors of this sort that are known for use in assays of aqueous fluids have demonstrated inadequate sensitivity. Specifically, poor sensor performance is attributed at least in part to the small size of the sample being analyzed, which is typically a few monolayers deep, and to the small active surface area of the optical waveguide. These factors limit the number of fluorophores that may be excited. More serious sensor performance degradation is attributable to the effects of a weak evanescent wave that fails to excite enough fluorophores to produce detectable levels of fluorescence. In addition, the past geometries used provide inadequate coupling of the fluorescence into the waveguide for subsequent detection.

Increasing the strength of the evanescent wave penetrating into a fluid sample to be assayed increases the amount of fluorescence, thereby increasing sensor sensitivity. Each mode (low and high order) propagating in the fiber has a portion of its power in the evanescent wave. Higher order modes have a larger percentage of their power in the evanescent wave and thus make a larger contribution to power in the evanescent wave. However, these higher order modes are weakly guided and lossy and can easily leak at a discontinuity or a bending point along the waveguide. In addition, the light distribution among the many modes of a multimode fiber is a very sensitive function of the specific optical arrangement of the fiber and effects on it produced by its environment. Even small bending or other mechanical effects on the fiber change the modal intensity distribution. These effects make an evanescent field sensor based on multimode fibers noisy and less sensitive.

The use of some types of tapered optical fiber to increase the sensitivity of fiber-optic assay systems is known. For example, it is known to use optical fibers as sensors in conjunction with assays.

Evanescent sensors using acid-etched multimode fiber probes are known. Higher-order modes in these fibers have the advantage of a large number of reflections per unit length and, thus, a long interaction length with the external medium and weaker evanescent field interaction to minimize photobleaching in situations where this might be a problem. However, the use of multimode fibers has a number of disadvantages. In a multimode sensor arrangement, the lower-order modes are confined to the central core region, limiting their interaction with the surroundings. This means that the total fraction of power that interacts with the external medium depends on the distribution of modal excitations and the fraction of each mode outside the core. Also, sensors made of multimode fibers are not easily compatible with many in-line fiber components, such as fiber directional couplers, isolators, and fiber Bragg grating filters.

Tapered multimode fibers may be produced in a known way using concentrated hydrofluoric acid (HF) solution. The method involves a multi-step procedure and requires a high-precision, computer-controlled stage to lower the fiber into the acid bath over a number of time intervals. This is a time-consuming and potentially non-reproducible procedure. In the procedure, the plastic cladding of the fiber is mechanically removed. This introduces a step discontinuity between the cladded and uncladded section of the fiber. Consequently, a combination tapering procedure is required to minimize V-number mismatch and prevent excess loss of returned fluorescence radiation through the tapered fiber. Such a procedure is potentially dangerous because of the use of hazardous chemicals such as concentrated HF acid. The tapering operation must be performed under a fume hood in a clean-room environment by well trained technicians.

Use of a single-mode fiber for sensing can avoid negative aspects of multimode fibers while having advantages such as light launched into the fiber exciting only the fundamental mode, which interacts with the surrounding area in the tapering region.

Optical fibers can also be tapered by heating and drawing, whereby both the core and cladding outer diameters are decreased and ultimately merge. One such tapered optical fiber is used in microscopy applications. The tapered fiber tip is short, has an extremely small diameter (a few tens of nanometers), and has a metal coating applied over the end of the tip.

When an optical fiber is tapered by heating and drawing, both the core diameter and the cladding outer diameter are decreased. The fractional change in the core diameter is approximately equal to the fractional change in the cladding outer diameter. In other words, the cross section of the fiber changes in scale only. Significantly, the angle at which the core is tapered is substantially smaller than the taper angle β, which is defined as the angle at which the drawn fiber is tapered. In one known example, the tangent of the core is only 3/125, or 2.4%, times the tangent of the taper angle β. For this reason, even for relatively large values of β such as 30° or greater, the core will have an adiabatic taper, as discussed below. When a fiber is drawn to a diameter comparable to, or smaller than, a wavelength, the boundary between core and cladding glass disappears and the structure becomes one of a glass core/fluid cladding.

In an untapered fiber, the electric component of the dielectric mode is largely confined to the core and falls to a very small amplitude, typically less than $10^{-10}$ times the peak amplitude, near the cladding outer surface. That is not necessarily the case in a tapered fiber. As a guided light wave propagates into the taper region, it encounters a progressively narrowing core. Eventually, the core becomes too small to substantially confine the guided mode. Instead, the light is guided by the interface between the cladding and the surrounding material, which may be air or a liquid. The core will generally be tapered at a small enough angle for the guide change to be adiabatic. By the term "adiabatic" it is meant that substantially all of the energy of the initial fundamental guided mode remains concentrated in a single mode, and is not coupled into other modes, particularly radiation modes, which lead to a loss of energy from the waveguide.

One potential disadvantage of fluorosensors is their use of fluorophores whose excitation and emission wavelengths are close to each other. It is very important to filter out the excitation light at the receiving port. Commonly, one or more low-pass filters (LPF) are placed in the return path to block the stray excitation light. However, commercially available dielectric LPF's do not have a sharp enough lower wavelength spectral characteristic and therefore cannot block the stray signal aft efficiently. Furthermore, previously known bulk optics arrangement using an off-axis perforated parabolic reflector are very costly and require crucial optical alignment. Photobleaching of the fluorophore when exposed to continuous laser irradiation in many sensors remains a serious problem and severely restricts fluorosensor sensitivity. In addition, in sensors using bulk optics, the large size, number of optic components that must be carefully aligned, and overall bulk of current fluorosensors makes them unsuited for general and widespread use.

SUMMARY OF THE INVENTION

An object of the invention is to provide a detector that overcomes the above-noted deficiencies.

Another object of the invention is to provide a detector that has a variety of applications in the fields of biology, biochemistry, chemistry, pharmacology and in many clinical applications.

To these and other objects, the present invention is directed to a probe for detecting a chemical, the probe comprising: an optical fiber having a tapered portion in which a diameter of the optical fiber is reduced from a larger diameter to a smaller diameter; and a coating disposed on a surface of the tapered portion of the optical fiber, the coating having a property of binding with the chemical when brought in contact therewith. The tapered fiber is held in a mechanical holder that is specially treated to prevent its reacting with any of the material that the treated fiber is designed to detect. The holder can also be placed in or made part of a flow cell with separate ports for entry and exit of fluid. Detection by the fiber can take place as fluid streams over the sensor.

The present invention is further directed to a method of making a probe for detecting a chemical, the method comprising: (a) forming a tapered portion in an optical fiber so that a diameter of the optical fiber is reduced in the tapered portion from a larger diameter to a smaller diameter; and (b) applying a coating on a surface of the tapered portion of the optical fiber, the coating having a property of binding with the chemical when brought in contact therewith.

The detector according to the present invention uses a tapered fiber to excite fluorescence from surface bound fluorophores and to couple the fluorescence back into the fiber. The fluorescence arises from species binding on the fiber surface resulting from the interaction (chemical, biochemical, bioaffinity, or immunogenic-type) of biomolecules (ligands) with their respective binding partners. The terms "ligand" and "binding partner" for the ligand are used to represent the two components in specific bioaffinity binding pairs, all of which are capable of recognizing and binding with the other partner in a biomolecular recognition pair. Examples of such binding pairs include: antigen-antibody, substrate-enzyme, effector-enzyme, inhibitor-enzyme, complementary nucleic acid strands (RNA or DNA), binding protein-vitamin, binding protein-nucleic acid, reactive dye-protein, reactive dye-nucleic acid, receptor-agonist or antagonist, and others.

Each of the binding partners is firmly attached to the tapered fiber surface and within the evanescent field. Coupling of sources outside the fiber core by evanescent field excitation has been predicted by a wave model of the light interaction. Fluorescence is efficiently excited or collected only from species that are in close proximity to the sample.

If a dye is immobilized at the fiber core interface, the structure serves as a sensor for the factors affecting its fluorescence parameters. When moieties with specific binding sites are immobilized on the surface as well, the unit senses a change in the excitation of the fluorophore. The overall sensitivity of the structure depends on the modes of light propagating in the fiber, the residual thickness of the cladding, and the chemical interaction between the fluorophore and the immobilized binding sites. To gain maximum access to the evanescent field and to enhance the detection sensitivity, a portion of the fiber cladding is removed.

The invention disclosed herein is directed in at least one embodiment to an all-fiber fluorescent sensor using a relatively long, adiabatically tapered, single-mode fiber probe. The fiber is mounted in a commercial micropipette puller. The fiber is heated before and during the drawing. A carbon dioxide ($CO_2$) laser is used as the heat source. By focusing the $CO_2$ laser beam on the fiber and controlling the pulling force and velocity with the micropipette puller, a highly reproducible, adiabatically tapered fiber can be drawn. The tapering angle can be adjusted by changing the pulling rate, pulling force, and laser beam spot size.

Adiabatic tapering provides efficient channeling of radiation into a fiber tip region where high amplitude evanescent field will be available for excitation of fluorophores.

BRIEF DESCRIPTION OF THE DRAWINGS

A preferred embodiment of the present invention will now be set forth in detail with reference to the drawings, in which.

DETAILED DESCRIPTION OF THE PREFERRED EMBODIMENTS

Figure 1:
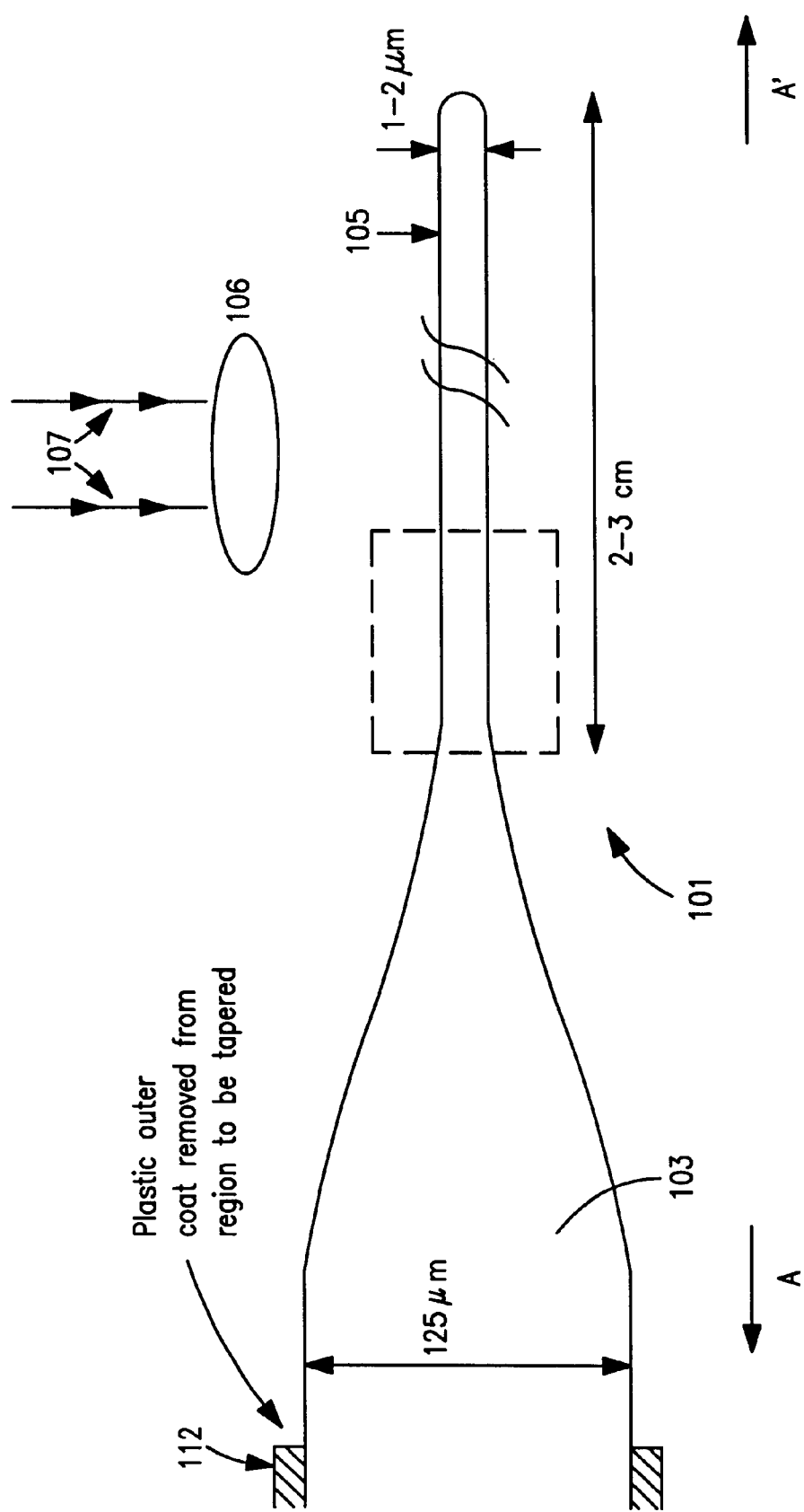
FIG. 1 shows a long, adiabatically tapered fiber used in the present invention.
Figure 1A:
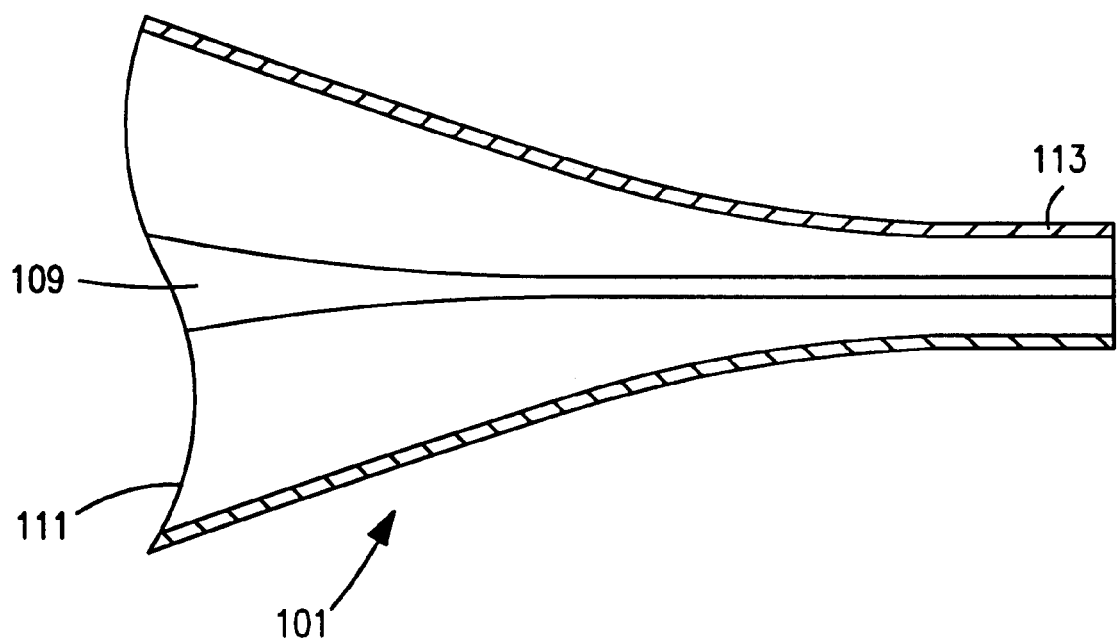
FIG. 1A shows an enlargement of a portion of the fiber shown in FIG. 1.

FIGS. 1 and 1A show a schematic of a long, adiabatically tapered fiber 101 produced by heating and drawing. The heating and drawing are implemented by using a cylindrical ZnSe lens 106 which focuses the high power laser beam 107 into a line image on the fiber 101 and holding one of the arms of the micropipette puller (not shown) stationary. This allows pulling in the direction indicated by arrow A or A' and thus the drawing of tapered fibers of relatively long length (typically a few centimeters). These long, single-mode fibers have a relatively small diameter (e.g., a few micrometers) along a substantial part of their tapered length. For example, as shown in FIG. 1, fiber 101 varies in diameter from 125 $\mu$m at wide portion 103 to 1–2 $\mu$m at narrow portion 105.

As shown in the enlargement of FIG. 1A, the fiber includes core 109 and cladding 111. The outside of the fiber is coated with a protective layer 112, normally made of plastic. This protective layer is removed from the region to be tapered so as to permit bonding of the sensing material of interest 113 to the tapered core/cladding region.

Figure 2:
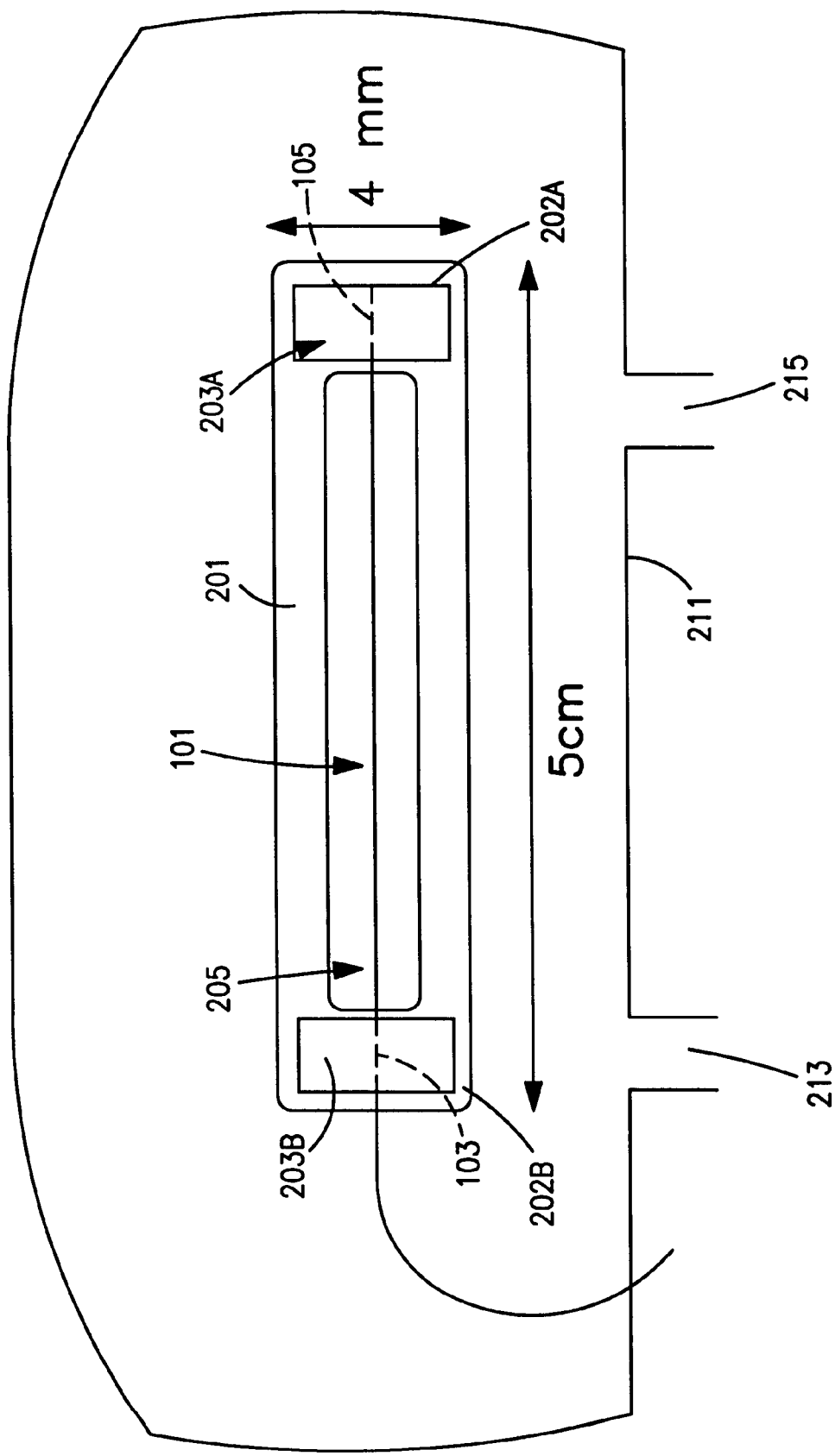
FIG. 2 shows a tapered fiber holder used in the present invention.

FIG. 2 shows a holder 201 used to prevent the fiber 101 from bending, breaking, or sticking to the walls of a flow cell (not shown). The holder 201 can be made of metal, such as aluminum, or a polymer such as polytetrafluoroethylene (sold under the trade name Teflon), depending on the types of chemicals used for treating the fiber surface. The tapered end 105 of the fiber 101 is glued to one end 202A of the holder 201 by mounting pad 203A, and the untapered section 103 of the fiber 101 is glued to the other end 202B of the holder 201 by mounting pad 203B, so that the tapered portion of the fiber is held within tapering region 205. As shown in FIG. 2, a fiber held this way remains straight, rugged, and easy to handle. In operation, the tapered fiber and its holder are placed into a flow cell (not shown), and a sample to be tested (also not shown) is injected into the flow cell.

The probe can be disposed in flow cell 211 having separate entry port 213 and exit port 215. Of course, another flow cell could be used, or the probe could be used without a flow cell (e.g., inserted into a body cavity).

Tapered fibers prepared in this fashion can be made so much more inexpensively than in prior art arrangements that they can easily be treated as disposable. Glass tapered fibers also have the advantage that materials bound to their surfaces can be easily removed and, in principle, the surface regenerated for further usage. Materials can be adhered to the surface of the tapered fiber. The fiber can be inserted into a liquid, gaseous, or solid environment in either a protected or unprotected fashion for real-time or delayed sensing either on-site or by remote signaling.

Such fibers can, for example, be used to detect airborne biological agents; monitor pH, temperature, or other changes in situ after insertion into a living organism or into a cavity in a solid mass such as wood; or placed directly into an on-stream effluent. Various chemical and biological materials can be adhered to the chemically modified tapered fiber surface, including dyes that fluoresce in response to biological activity of fungi or other microorganisms, pH, or temperature changes, or in response to interactions between biological molecules such as RNA, DNA, or proteins. These interactions include antibody-antigen recognition and DNA or RNA strand recognition. Assays include sandwich-type immunoassays and hybridization assays as well as mixed assays in which an antibody or other protein or some other agent captures a nucleic acid probe that then participates in a sandwich or other type of biological recognition assay.

The dyes may be attached to the surface of the tapered fiber, covalently attached to a molecule interacting at the surface of the fiber, or noncovalently attached to molecules interacting at the tapered fiber surface, such as ionic adherence of a dye to a protein molecule or intercalation of a dye between two strands of a nucleic acid. Concomitantly, assays can be structured so that a fluorophore bound to a carrier agent is displaced and the extent of displacement is proportional to the presence of the agent to be measured. Fluorescence signal intensity can be modified either by the absence or variable concentration of fluorophore present or by the attenuation of a standard fluorescence signal from a fluorophore when another reagent enters the detection environment. In addition fluorescence can be enhanced by the presence of a second fluorophore that when excited causes radiationless energy transfer to the first fluorophore which then in turn emits light of even longer wavelength than it does after absorbing light that causes direct excitation. Also, the fluorescence from a surface-bound fluorophore can be spectrally modified by species-specific surface binding.

Detection of evanescent wave interactions with the fluorophore can include interferometric comparisons of absorption of light energy by a sample compared with a standard, interferometric comparison of light emitted by a fluorophore, wave-coupling between two closely adjacent optic fibers, and direct measurement of light emitted by a fluorophore back through or forward into an optical fiber.

A laser or laser diode that emits light radiation of between 600 and 1600 nm can be used to excite the fluorescence from moieties either attached to or located within the range of the evanescent wave emanating from the tapered region of the fiber probe. Near infrared fluorophores whose excitation and emission spectra peak in the near infrared region are particularly desirable for examining clinical and other biological samples because naturally occurring materials in this region of the spectrum show no fluorescence when illuminated with infrared electromagnetic radiation.

Figure 3:
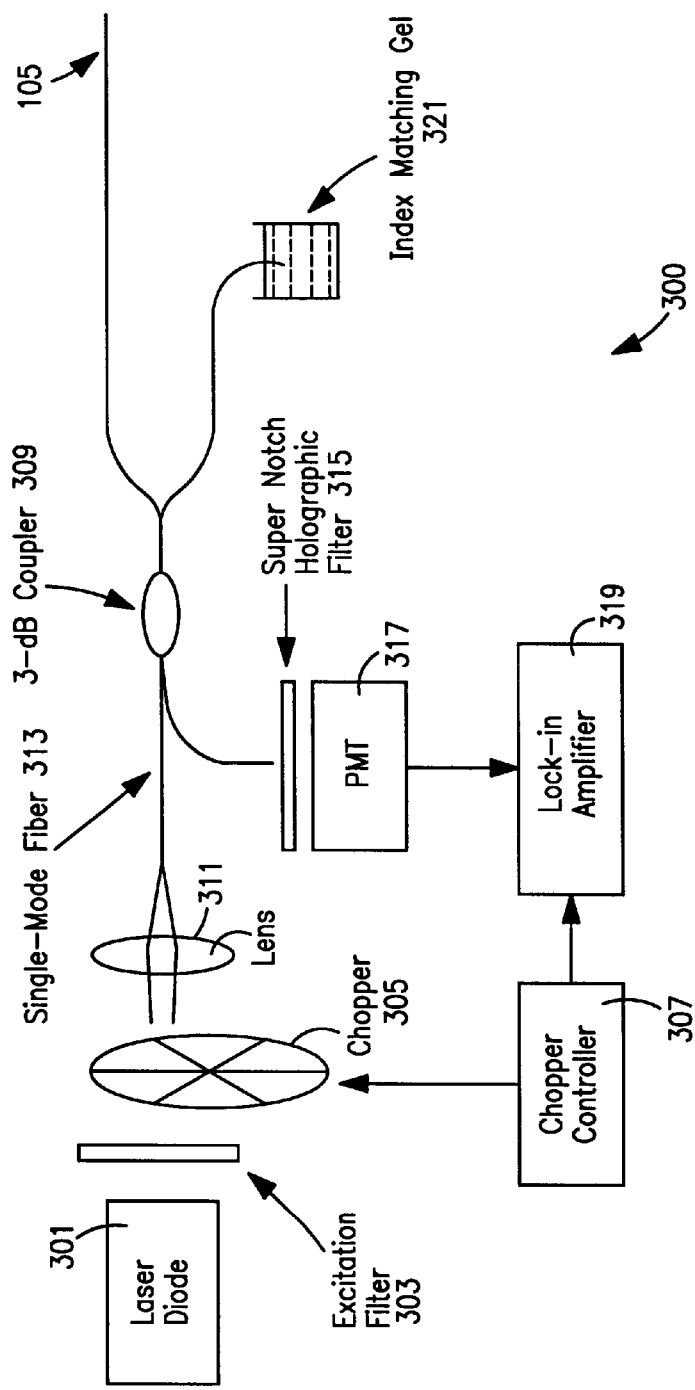
FIG. 3 shows an exemplary embodiment of a fiber-optic fluorosensor according to the present invention.

A schematic of the fiber optic fluorosensor 300 is shown in FIG. 3. A 785-nm laser diode 301 is used to excite the fluorescence in the tapered region of the fiber probe. The laser dye used may be an IR-125 (Lambda Physik) or an IRD-41 (Li-Cor), with excitation wavelengths around 795 and 787 nm, respectively, and emission wavelengths around 830 and 807 nm, respectively. Other cyanine or non-cyanine dyes can also be used. An excitation filter 303 is used to block unwanted background light from the laser diode source. A chopper 305 under the control of chopper controller 307 is employed to facilitate lock-in detection and hence improve the sensitivity of the sensor. The laser light from laser diode 301 is coupled into a 3-dB fiber directional coupler 309 via a biconvex silica lens 311 and single-mode fiber 313. The fiber 313 is angle cleaved at the input port to remove the 4% back reflection that results at glass-air interfaces. This angle cleaving eliminates the need for a conventional bulk optics arrangement using an off-axis parabolic reflector; such a conventional bulk optics arrangement is very costly and requires crucial optical alignment. The fluorescence originating from the tapered end 105 of the fiber is directed by the fiber coupler 309 through filter 315, such as a SuperNotch™ holographic filter (SNHF), and into a photomultiplier tube (PMT) 317. The output of PMT 317 is applied to lock-in amplifier 319. The remaining port of coupler 309 is supplied with index-matching gel 321.

To overcome the problem of using a fluorophore in which the excitation and emission wavelengths are close to each other, an SNHF that operates at 785 nm was obtained from Kaiser Optical Systems, Inc., and used as filter 315. These filters are currently being used by researchers for dispersive and FT-Raman spectroscopy. SNHF's are fabricated using dichromated gelatin, and their use confers the advantages of high laser attenuation, narrow spectral bandwidth, sharp band edges, uniform high transmission outside the notch region, and wide wavelength range. The SNHF 315 should preferably be placed in the path of a collimated beam to obtain the best performance. This underscores the importance of using a fiber coupler to carry the return signal rather than using an off-axis parabolic mirror to focus the return beam.

Figure 4:
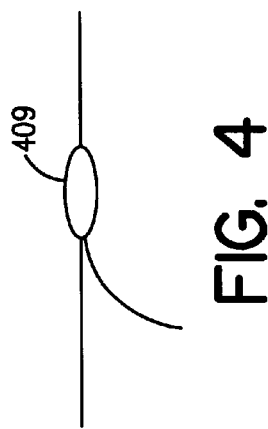
FIG. 4 shows an alternative coupler for use in the fiber-optic fluorosensor of FIG. 3.

The 3-dB (2×2) fiber coupler 309 shown in FIG. 3 can be replaced by a 2×1 or other coupler with the desired power-splitting ratio, such as coupler 409 shown in FIG. 4. In fluorophore applications, it is important to attenuate the excitation signal to reduce photobleaching, but it is desirable to collect the maximum fluorescence. This can be done by choosing a proper power-splitting ratio among the ports of the 2×1 coupler 409. Unlike coupler 309 of FIG. 3, coupler 409 does not require any index matching for the unused port (e.g., to avoid back reflection).

Figure 5:
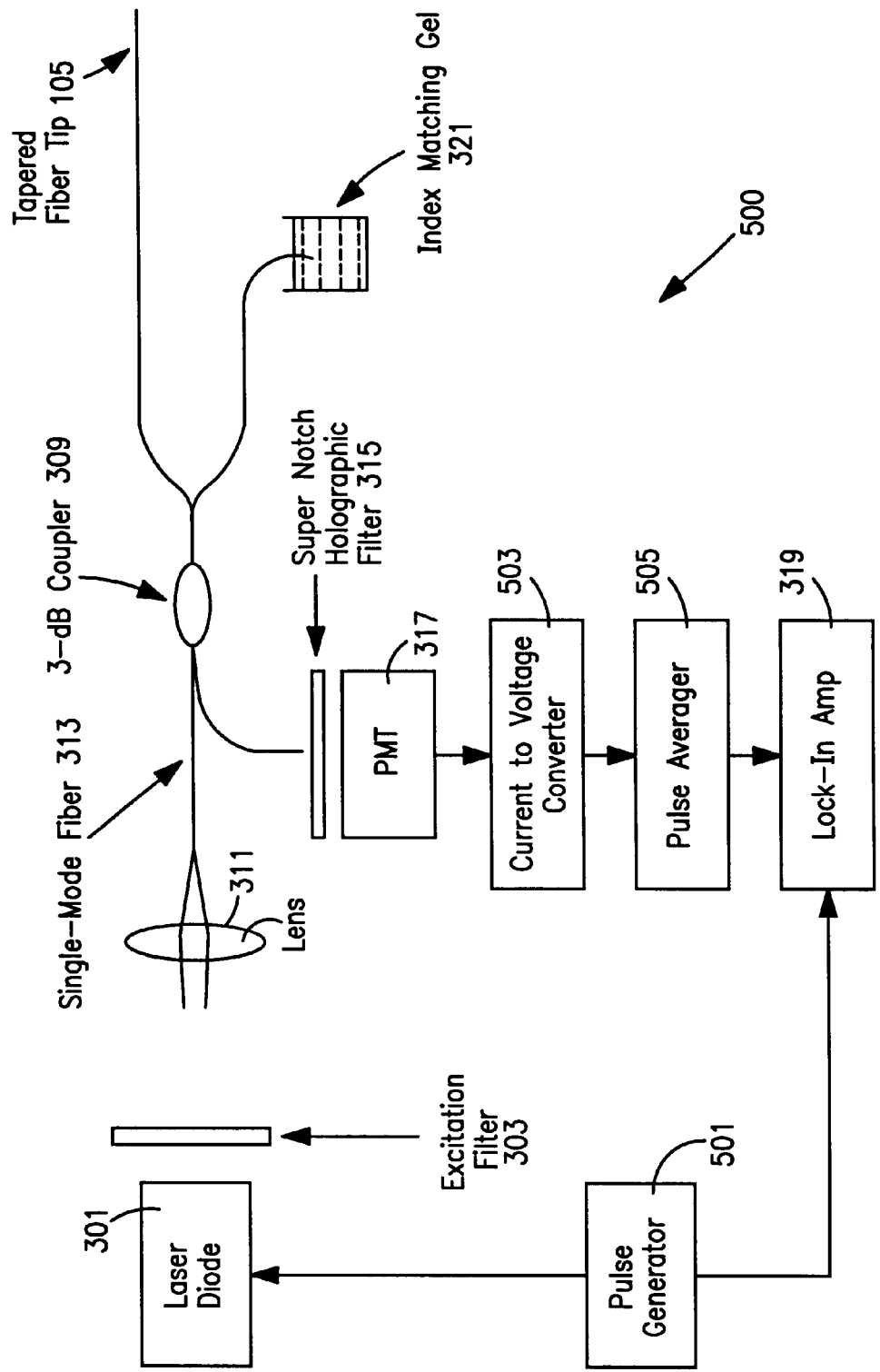
FIG. 5 shows another exemplary embodiment of a fiber-optic fluorosensor according to the present invention.

For dye immobilized at the end of the tapered fiber, there may only be a limited amount of light which can be measured before the immobilized dye is bleached. To enhance the signal-to-noise (S/N) ratio and to minimize the photobleaching effect, a pulse-mode detection arrangement rather than a continuous wave (CW) operation is employed, as shown in FIG. 5. Fluorosensor 500 of FIG. 5 differs from fluorosensor 300 of FIG. 3 in the following respects. First, laser diode 301 is modulated by pulse generator 501. Accordingly, chopper 305 and chopper controller 307 can be dispensed with. Second, signals output by PMT 317 are supplied to current-to-voltage converter 503 and thence to pulse averager 505, which averages over the pulses under the control of pulse generator 501, before being supplied to lock-in amplifier 319.

In this arrangement, the laser diode 301 which is externally modulated by pulse generator 501 sends pulses of short duration to the sensing region. The resulting fluorescence signal is amplified by lock-in amplifier 319, which provides a larger absolute signal level. This arrangement also allows the possibility of timed injection of samples to be tested and time-synchronous observation of fluorescence after sample injection.

An additional modification to enhance the S/N ratio and minimize photobleaching is to conduct the measurements of the fluorosensor in a nonaqueous or semi-aqueous environment using various polar and nonpolar organic reagents.

To test the performance of the fluorosensor according to the present invention, near infrared and other dyes have either been attached physically or chemically to the surface of the tapered fiber, covalently or noncovalently attached to a biomolecule that was then chemically or physically attached to the tapered fiber surface, or added in the form of a solution of the fluorophore into which the tapered fiber was immersed.

Various treatments can be used to prepare the tapered fiber surface. The surface can be cleaned first by heating with acids and/or oxidizing agents and other reagents. The cleaned, tapered fiber is then immersed in aqueous or nonaqueous solutions containing mercapto or other types of silane or other reagents and treated either with or without heat for several hours. After extensive washing, the fibers are dried at high heat in an oven for several hours minimum. At this stage fluorescent dyes can be noncovalently attached to the surface.

To covalently attach biological or other materials to the surface, further treatment of the tapered fiber surface is desirable after heating in the oven. The treated fibers are further reacted with organic reagents such as dialdehydes, heterobifunctional crosslinkers, or other chemical reagents. After extensive washing of the surface the fibers are ready for further use. Biological materials such as nucleic acids or proteins are placed in contact with the surface for periods ranging from one to several hours either at room temperature or in the cold.

To initially monitor the steps and conditions for preparing the fiber surface, preliminary experiments were conducted with thick borosilicate glass slides containing a pair of ground and polished concavities. The slides were treated with a variety of conditions and reagents and tested with fluorescein dye either free in solution or covalently attached to a biological molecule. Reactivity of the dye with the glass was monitored by examination with an epifluorescence microscope.

Examination by epifluorescence microscopy revealed, for example, that (1) free fluorescein dye could attach to silane-treated glass surfaces but could not attach after the silane-treated surface was further modified with dialdehyde, heterobifunctional, or other reagent and (2) that an oligonucleotide containing covalently attached fluorescein bonded to silane-treated surfaces both before and after further treatment with chemical reagents. Oligonucleotide bound to silane-treated surfaces alone, however, was not available for hybridization with a complementary strand. In addition, chemical modification of the oligonucleotide structure was also necessary for the proper attachment of the oligonucleotide to the chemically treated, tapered fiber surface so that hybridization could occur.

Using the fluorescein experiments as a guide, appropriately treated tapered fibers were immersed for several hours in solutions of near infrared dyes and then washed extensively. Signal was obtained from fibers washed free of dye indicating that dye was adsorbed to the fiber surface. In other experiments, treated fibers were immersed in solutions of near infrared dye and uptake of the dye to the tapered fiber surface was monitored by intermittently measuring the signal of dye bound to the tapered fiber surface. A linear increase in signal with a relatively shallow slope was obtained.

Hybridization reactions were conducted using treated tapered optic fibers and the instrument configuration shown herein. Target oligonucleotide was covalently attached to the chemically modified surface of tapered optic fibers. Hybridization reactions were conducted at elevated temperatures using Denhardt's solution and buffered standard saline citrate. A probe molecule containing covalently attached fluorophore was used to determine when specific binding occurred.

For example, pre-hybridization solution consisted of 5× standard saline citrate (0.75 M NaCl, 0.075 M sodium citrate, pH 7.0); Denhardt's solution [0.1% Ficoll (400,000 mol. weight), 0.1% polyvinyl pyrollidone (400,000 mol. weight), and 0.1% bovine serum albumin], 0.005 M sodium phosphate buffer, pH 6.8, and Tween 20 (1 ml/liter) heated to 65° C. Fibers were washed twice in this buffer. Hybridization was carried out by adding 0.2–20 pmol/ml of 20-mer oligonucleotide, containing IRD-41 near infrared fluorophore attached to the 5'-end, to fresh pre-hybridization solution and heating to 65° C.

Figure 8:
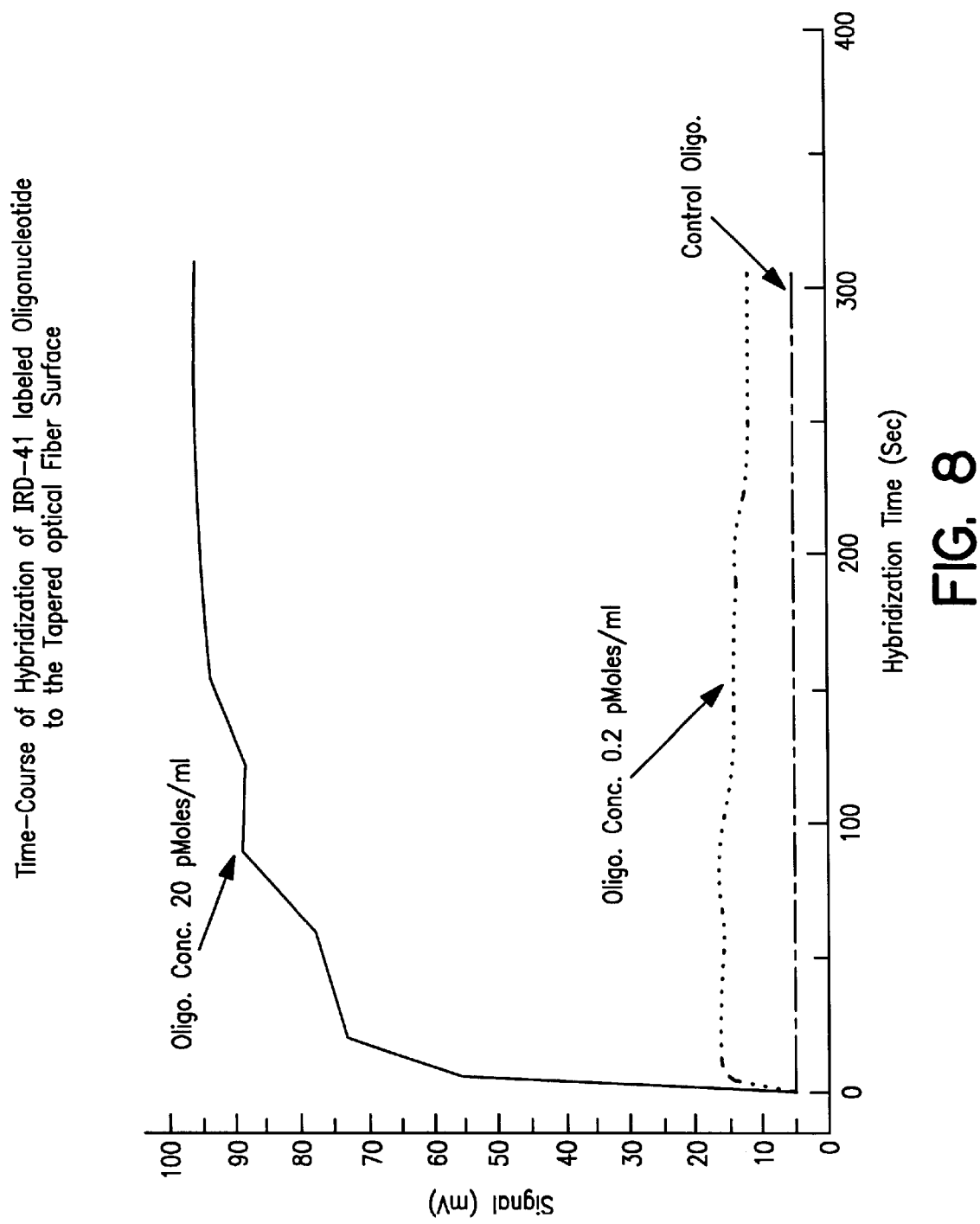
FIG. 8 shows results of hybridization with 20, 2 and 0.2 pmol/ml of probe.
Figure 9:
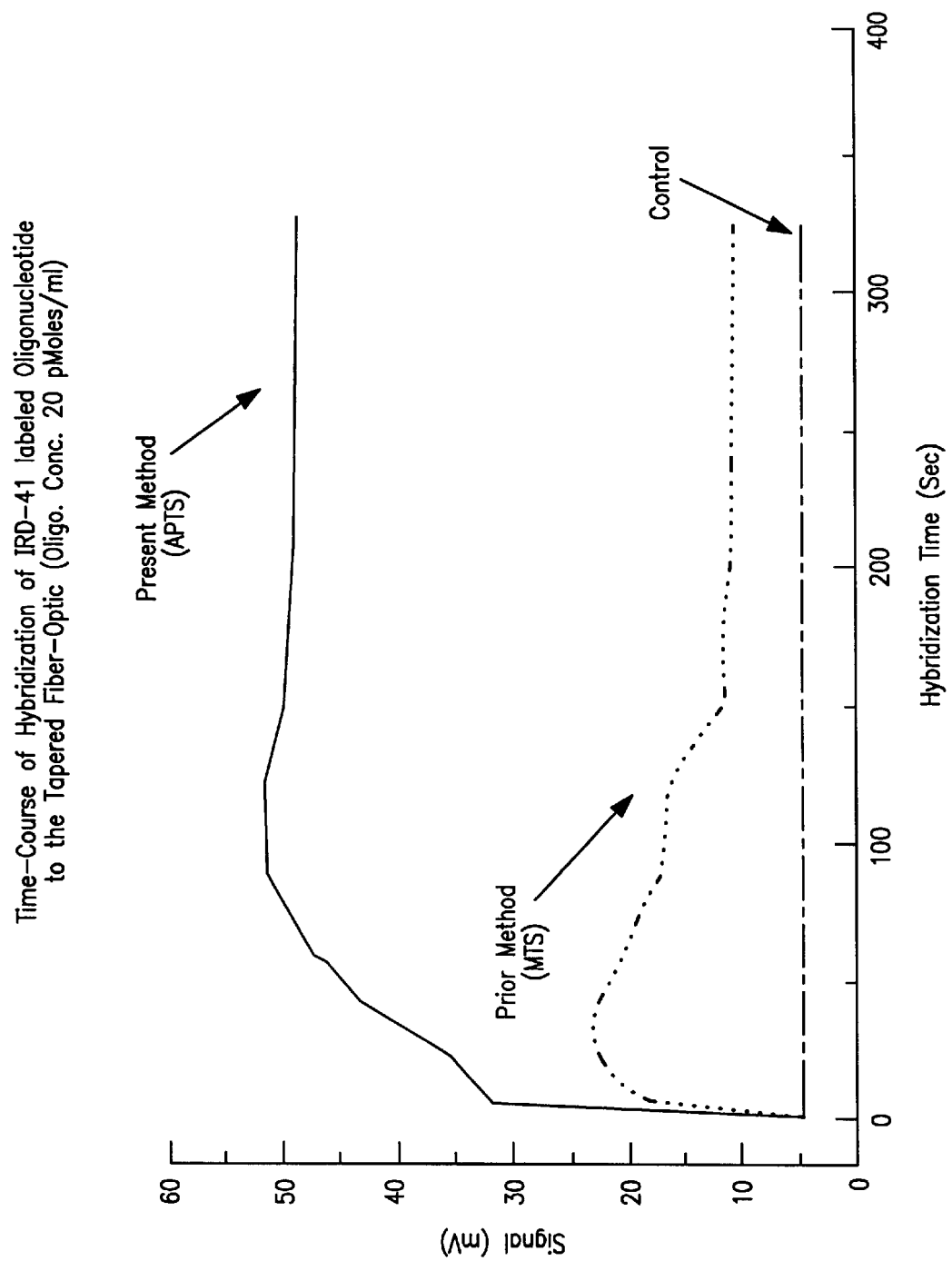
FIG. 9 shows hybridization with fibers treated according to the present invention and according to a known technique.

The results obtained are shown in FIGS. 8 and 9. FIG. 8 shows hybridization with 20 and 0.2 pmol/ml of probe. FIG. 9 compares hybridization with two probes, one prepared with the aminopropyltriethoxysilane (APTS) procedure (marked as "PRESENT METHOD") and the other with the 3-mercaptotrimethoxysilane (MTS) procedure (marked as "PRIOR METHOD") (both to be described below).

Such an assay could be used to detect the presence or absence of bacteria, fungi, other microorganisms, viruses, or specific genes for identification of infectious or other disease based on the presence of either specific DNA or RNA. Similar assays can also serve to narrow selection of specific genetic sequences or to identify a known or unknown sequence from any source.

Antibody-antigen sandwich-type immunoassays were conducted by attaching a protein, in this case serum albumin, to the surface of chemically treated tapered fibers. Mouse monoclonal antibody specific for recognition of serum albumin was added. Detection was carried out by then adding a second antibody, to which a fluorophore had been noncovalently attached and free dye removed, that could recognize the presence of the monoclonal protein.

Either hybridization or immunoassays could be used to determine the presence of specific antibody or other protein; monitor growth; analyze deterioration of wood or other structures, foods, and other materials; determine response to drug or other therapy; monitor specific biological processes; detect the presence or absence of harmful or benign biological and/or chemical agents; detect enabling or destructive substances in agricultural, industrial, and home products and/or processes; and monitor and detect pollution in air, water, and/or soil.

In another alternative, pH-sensitive dye was attached to the chemically treated surface of a tapered fiber.

The fluorosensor described here confers the added advantage of being unusually sensitive to the detection of free or attached fluorophore. For example, nM concentrations or less and $10^7$ molecules bound to the surface of an optic fiber with dimensions of typically 2 cm×2–3 µm. The system described here by immersing the tapered end of a fiber into a solution of IR-125 provides a signal from on the order of $10^7$ molecules within the evanescent field range of the solution surrounding the tapered tip. The system has very large dynamic range limited only by the dynamic range of available sensitive photodectors, which can be linear over eight orders of magnitude, and the capability of changing the excitation laser intensity.

Figure 6:
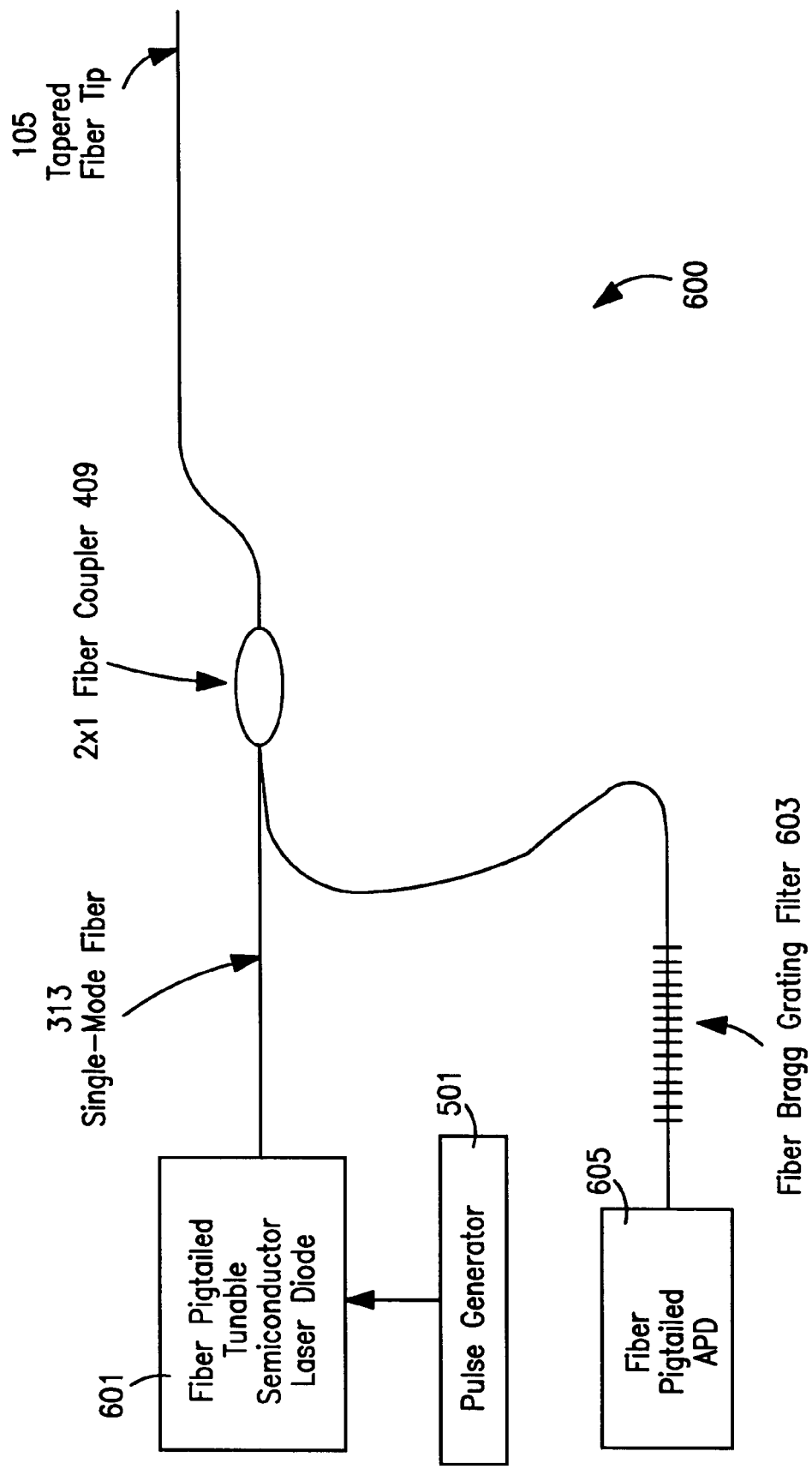
FIG. 6 shows yet another exemplary embodiment of a fiber-optic fluorosensor according to the present invention.

A way to make the present fluorosensor system more compact and rugged is to make it an all-fiber system in which all the optical elements are replaced by in-line fiber components. An example of such an all-fiber system is system 600 of FIG. 6. This allows the use of a tunable fiber pigtailed semiconductor laser 601 under control of pulse generator 501. Through proper tuning of the laser wavelength emitted by laser 601, the use of a bulk optic excitation filter can be avoided, and also the light-launching efficiency is maximized without any need for a fiber launcher and focusing optics.

In this respect, the fiber-optic coupler 309 or 409 is preferable in making an all-fiber evanescent wave sensor. A 1×2 or 2×2 port fiber-optic directional coupler with the appropriate coupling ratio can be spliced to the fiber pigtailed to the light source. The output port of the coupler is spliced to a tapered fiber probe (sensing head) 105 which has been placed inside the flow cell. Now, instead of using a SNHF to block the stray excitation light and a PMT to detect the fluorescence, a Fiber Bragg Grating Filter (FBGF) 603, explained in detail below with reference to FIG. 7, may be added, and a fiber pigtailed Avalanche Photodiode Detector (APD) 605 may be used instead.

Figure 7:
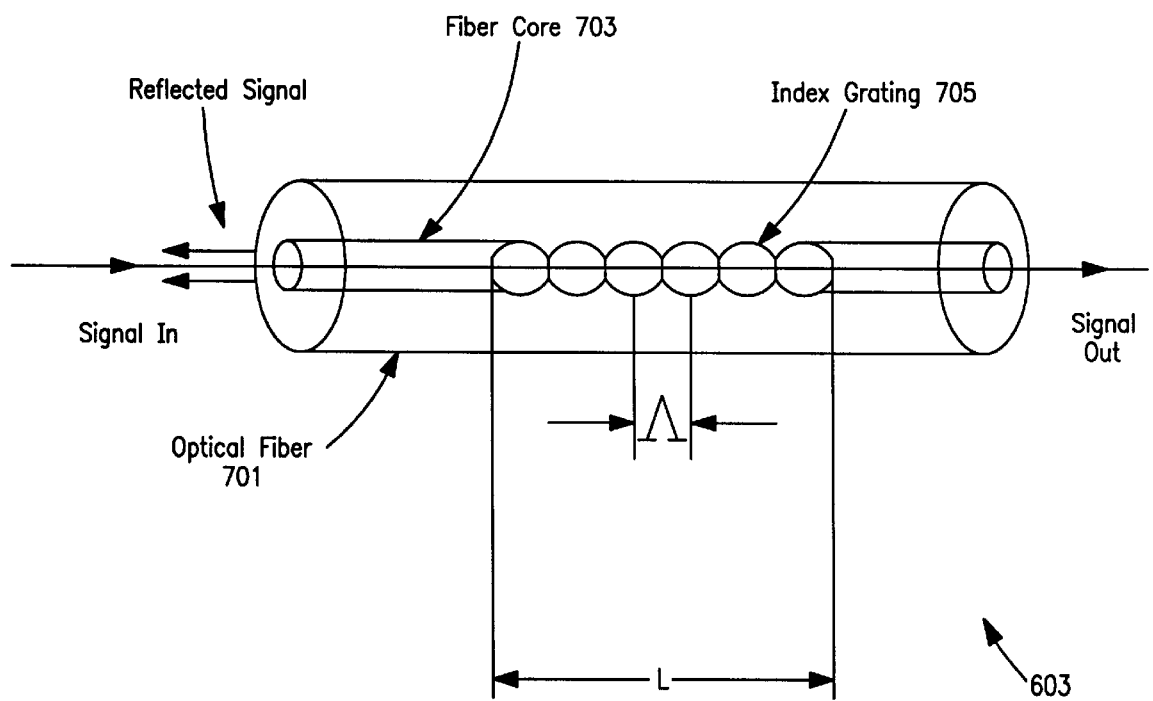
FIG. 7 shows a fiber-optic Bragg grating used in the fiber-optic fluorosensor of FIG. 6.

As shown in FIG. 7, fiber Bragg grating 603 is made by exposing the core 703 of a single mode fiber 701 to a spatially periodic pattern of intense ultraviolet light. The exposure produces a permanent increase in the refractive index of the fiber's core, creating an index modulation by the exposure pattern. This index modulation produces an in-fiber Bragg grating 705 having length L. Incident light at the Bragg wavelength is reflected back and propagates against the incident light direction. The wavelength at which this reflection occurs is referred to as the Bragg wavelength and is given by $$\lambda_B = 2 n_e \Lambda,$$

where $\lambda_B$ is the wavelength at which reflection will be obtained, $n_e$ is the effective average index of refraction of the core, and $\Lambda$ is the Bragg grating spacing.

Fiber Bragg gratings are unique in that they are all-fiber components capable of performing as wavelength selective filters. Almost all propagating wavelengths pass through the grating with negligible insertion loss and no change in signal. Only those wavelengths that satisfy the Bragg condition are affected, in which case they all add coherently and are strongly reflected back. Hence, a fiber Bragg grating acts as a notch filter by retro-reflecting a band from the incident spectrum. Bragg grating wavelength tuning is achieved by changing the grating period spacing, which can be accomplished through either mechanical or thermal means.

The disclosed embodiment of the invention includes the following features and advantages. A highly sensitive, all-fiber fluorosensor has been constructed and tested that uses semiconductor laser excitation and infrared fluorophores. The sensor includes highly reproducible, long adiabatically tapered optical fibers. The fibers are fabricated using a carbon dioxide laser, micropipette puller, and an infrared lens that focuses the beam into a line image on the fiber. The instrument configuration incorporates a SuperNotch Holographic Filter to overcome the problems inherent with the use of one or more low-pass filters. To enhance the signal-to-noise ratio and minimize photobleaching, a pulse detection system has been used. To further enhance the signal-to-noise ratio and minimize photobleaching, a nonaqueous or semi-aqueous environment using various polar and non-polar organic reagents is used.

Tapered fiber surfaces have been chemically prepared that are capable of physically and/or chemically binding a variety of dyes, other chemicals, and biological molecules. For example, as part of a standard procedure, fibers were cleaned by immersing in 5% nitric acid at 90° C. for one hour. After extensive rinsing with deionized water, fibers were transferred to a solution of 10% (v/v) of aminopropyltriethoxysilane (APTS) in water, pH 3–4, and heated for two hours at 75° C. After extensive rinsing with deionized water, the fibers were dried in a convection oven at 115° C. for a minimum of four hours. A 20-mer oligonucleotide containing a 5'-terminal amine group was added in phosphate-buffered saline to a concentration of 10 µg/ml. The fiber was then placed in this solution overnight at 4° C.

To compare alternative methods for preparing fibers, the following procedure was used. Fibers were initially cleaned with 5% nitric acid at 90° C. for one hour. After careful rinsing with deionized water, the fibers were allowed to air dry. Fibers were then treated with a 2% solution of 3-mercaptotrimethoxysilane in toluene under a $N_2$ atmosphere for two hours. Fibers were rinsed in dry toluene and allowed to air dry. A 1.7-mg portion of N-gamma-maleimidobutyryloxy succinimide ester (GMBS) was dissolved in 0.5 ml of N,N-dimethylformamide, which was then diluted to 3 ml final volume with absolute ethanol. Fiber surfaces were activated in this solution by immersion for one hour and then rinsed with phosphate-buffered saline. A 20-mer oligonucleotide containing a 5'-terminal amine group was then added in phosphate-buffered saline to a concentration of 10 µg/ml. The fiber was placed in this solution overnight at 4° C.

To guide these experiments, parallel experiments have been conducted with fluorescein dye, microscope slides with dual concavities, and epifluorescence microscopy. Examination of slide surfaces showed that free fluorescein dye was adsorbed to aminopropyltriethoxysilane treated (APTS) surfaces and that oligonucleotide carrying covalently attached fluorescein was attached to both APTS and glutaraldehyde-treated surfaces. Chemically treated optic fibers immersed in solutions of near infrared dye showed adsorption of dye to the fiber surface even after extensive washing. Uptake of near infrared dye was monitored over several hours and showed a linear increase with a relatively shallow slope. Analyses of the number of molecules of dye detected by these methods suggested a range of $10^7$ to $10^{14}$ molecules.

To prevent the material that the probe is designed to detect from being lost by chemical or physical binding to the mechanical holder rather than to the treated optical fiber, the holder is specially treated to prevent such binding. The fiber holder can be treated in different ways to prevent it from capturing material. One method of treatment is as follows:

1. The holder is treated with 5% nitric acid (v/v) for one hour at 90° C.
2. The holder is rinsed in deionized water and air-dried at room temperature.
3. The holder is then placed in a solution of acetone containing 1% (v/v) of ethyltriethoxysilane (ETS) at 85° C. and left there until the solution evaporates to dryness.
4. The holder is heated in a convection oven at 115° C. for about ten hours.

Other methods of surface treatment to prevent undesirable binding include similar general steps of cleaning, rendering the holder surface inactive with an appropriate chemical coating, followed by a curing process to ensure tight binding of the protective coating. Alternatively, a holder that is completely fabricated from a non-reactive material such as polytetrafluoroethylene (sold under the name Teflon) can also be used.

While a particular embodiment has been set forth in detail above, those skilled in the art who have reviewed this disclosure will readily appreciate that modifications can be made without departing from the invention. Also, the variations described above can be combined with one another or with such modifications as needed. Therefore, the invention should be construed as limited only by the appended claims.

We claim:

1. A method of making a probe for detecting a chemical, the method comprising:
    (a) forming a single tapered portion on one end in a single mode optical fiber so that a diameter of the optical fiber is reduced in the single tapered portion from a larger diameter to a smaller diameter; and
    (b) applying a coating on a surface of the tapered portion of the optical fiber, the coating having a property of binding with the chemical when brought in contact therewith.

2. A method as in claim 1, wherein the coating is sensitive to pH.

3. A method as in claim 1, wherein the coating is sensitive to temperature.

4. A method as in claim 1, wherein the probe detects a biological agent.

5. A method as in claim 4, wherein the biological agent is airborne and is sampled from the air and presented to the probe.

6. A method as in claim 4, wherein the biological agent is a product of biological activity of a microorganism.

7. A method as in claim 4, wherein the biological agent is a virus, a part of a virus, or product of a virus.

8. A method as in claim 4, wherein the biological agent is a fungus, a part of a fungus, or a product of a fungus.

9. A method as in claim 1, wherein the probe detects a chemical occurring in a living organism.

10. A method as in claim 1, wherein the probe detects, a chemical occurring in a cavity in a solid mass.

11. A method as in claim 1, wherein the probe detects, a chemical occurring in an on-stream effluent.

12. A method as in claim 1, wherein the probe detects an antigen; and the coating comprises an antibody to the antigen.

13. A method as in claim 1, wherein the probe detects an antibody; and the coating comprises an antigen to the antibody.

14. A method as in claim 1, wherein the probe detects intact DNA or a portion of DNA (oligonucleotide).

15. A method as in claim 1, wherein the probe detects intact RNA or a portion of RNA (oligonucleotide).

16. A method as in claim 1, wherein the coating is covalently attached to the surface.

17. A method as in claim 1, wherein the probe detects a chemical in a nonaqueous environment or a semiaqueous environment, so photobleaching is minimized.

18. A method as in claim 1, wherein the tapered portion is adiabatically tapered.

19. A method as in claim 1, wherein:
    the optical fiber comprises a core and a cladding; and
    a portion of the cladding is removed to expose the surface on which the coating is disposed.

20. A method as in claim 19, wherein the surface is on the core, whereby the coating is in contact with the core.

21. A method as in claim 1, wherein step (a) comprises heating and pulling the optical fiber.

22. A method as in claim 1, wherein step (b) comprises:
    (i) chemically treating the surface to increase an ability of the coating to adhere to the surface; and
    (ii) thereafter applying the coating to the surface.

23. A method as in claim 22, wherein step (b)(i) comprises treating the surface with a silane.

24. A method as in claim 23, wherein step (b)(i) further comprises heating the surface.

25. A method as in claim 23, wherein step (b)(ii) comprises addition of an additional chemical to the silane.

26. A method as in claim 25, wherein the additional chemical comprises glutaraldehyde.

27. A method as in claim 25, wherein the additional chemical comprises a heterobifunctional crosslinker.

28. A method as in claim 1, wherein the probe detects a chemical in solution.

29. A method as in claim 1, wherein the probe detects a chemical in a solid environment.

30. A method as in claim 1, wherein the probe detects a protein.

31. A method as in claim 30, wherein the protein is an enzyme.

32. A method as in claim 30, wherein the protein is a receptor.

33. A method according to claim 1, wherein a heat source is used for forming the tapered portion, and the heat source is a laser.

34. A method according to claim 33, wherein the laser is a $CO_2$ laser.

35. A method according to claim 1, further comprising:
   c) cleaning the surface of the fiber by heating with a chemical compound,
   d) immersing the fiber in one or more solutions containing at least one silane, and
   e) washing and drying the fiber.

36. A method of making a probe for detecting a chemical, the method comprising:
   (a) forming a tapered portion on one end in an optical fiber so that a diameter of the optical fiber is reduced in the tapered portion from a larger diameter to a smaller diameter; and
   (b) applying a coating on a surface of the tapered portion of the optical fiber, the coating having a property of binding with the chemical when brought in contact therewith,
   wherein the coating is ionically attached to the surface.

37. A method of making a probe for detecting a chemical, the method comprising:
   (a) forming a tapered portion on one end in an optical fiber so that a diameter of the optical fiber is reduced in the tapered portion from a larger diameter to a smaller diameter; and
   (b) applying a coating on a surface of the tapered portion of the optical fiber, the coating having a property of binding with the chemical when brought in contact therewith,
   wherein (b) comprises:
      (i) chemically treating the surface to increase an ability of the coating to adhere to the surface, and
      (ii) thereafter applying the coating to the surface;
   wherein (b)(i) comprises treating the surface with a silane, and wherein the silane comprises mercaptosilane.

38. A method of making a probe for detecting a chemical, the method comprising:
   (a) forming a tapered portion on one end in an optical fiber so that a diameter of the optical fiber is reduced in the tapered portion from a larger diameter to a smaller diameter; and
   (b) applying a coating on a surface of the tapered portion of the optical fiber, the coating having a property of binding with the chemical when brought in contact therewith,
   c) providing a holder for the probe, the holder being chemically treated to prevent binding of the chemical of b) to the holder.

* * * * *